United States Patent
Podoleanu

(10) Patent No.: US 7,594,730 B2
(45) Date of Patent: Sep. 29, 2009

(54) METHOD AND APPARATUS FOR DISPLAYING OCT CROSS SECTIONS

(75) Inventor: Adrian Podoleanu, Canterbury (GB)

(73) Assignee: OTI Ophthalmic Technologies Inc. (CA)

( * ) Notice: Subject to any disclaimer, the term of this patent is extended or adjusted under 35 U.S.C. 154(b) by 76 days.

(21) Appl. No.: 11/547,922

(22) PCT Filed: Mar. 11, 2005

(86) PCT No.: PCT/CA2005/000367

§ 371 (c)(1),
(2), (4) Date: Jun. 13, 2007

(87) PCT Pub. No.: WO2005/087088

PCT Pub. Date: Sep. 22, 2005

(65) Prior Publication Data

US 2008/0074617 A1   Mar. 27, 2008

(30) Foreign Application Priority Data

Mar. 11, 2004   (GB) ................. 0405416.9

(51) Int. Cl.
*A61B 3/00*   (2006.01)
*A61B 3/02*   (2006.01)
*A61B 3/10*   (2006.01)

(52) U.S. Cl. .................. 351/246; 351/237; 351/221

(58) Field of Classification Search .......... 351/205–246
See application file for complete search history.

(56) References Cited

U.S. PATENT DOCUMENTS

| 5,310,764 A * | 5/1994 | Baranowitz et al. ......... 514/725 |
| 6,769,769 B2 * | 8/2004 | Podoleanu et al. .......... 351/221 |
| 2007/0179512 A1 * | 8/2007 | Olsen et al. ................. 606/151 |

FOREIGN PATENT DOCUMENTS

| WO | WO 2003/011764 A2 | 2/2003 |
| WO | WO 2004/006751 A2 | 1/2004 |

OTHER PUBLICATIONS

Westphal, et al, "Correction of geometric and refractive image distortions in optical coherence tomography applying Fermat's principle;" Optics Express, May 6, 2002, pp. 397-404, vol. 10, No. 9, Optical Society of America.

Westphal, et al, "Quantitative OCT image correction using Fermat's principle and mapping arrays;" Proceedings of SPIE, 2002, pp. 54-58, vol. 4619, The International Society for Optical Engineering. May 6, 2002.

* cited by examiner

*Primary Examiner*—Mohammed Hasan
(74) *Attorney, Agent, or Firm*—Lawrence E. Laubscher, Jr.

(57) ABSTRACT

OCT cross section images of a part of a curved object are displayed by creating a series of image points and placing each image point into a corrected image in such a way that the positions of scattering points within the image coincide with or are at least closer to their real spatial distribution within the curved object.

17 Claims, 3 Drawing Sheets

Normal fovea

Neuronitis with optic disc edema and peripapillary serous detachment

Below the broken line, the unit length along the vertical coordinate is 10 times smaller than above the line.

METHOD AND APPARATUS FOR DISPLAYING OCT CROSS SECTIONS

FIELD OF THE INVENTION

This invention relates to the field of Optical Coherence Tomography (OCT), and in particular to a method of displaying OCT sections of the retina of the eye.

BACKGROUND OF THE INVENTION

Optical coherence tomography (OCT) is a powerful and sensitive tool for characterization of optical properties and imaging of superficial tissue, as described in the paper by D. Huang, E. A. Swanson, C. P. Lin, J. S. Schuman, W. G. Stinson, W. Chang, M. R. Hee, T. Flotte, K. Gregory, C. A. Puliafito and J. G. Fujimoto, 'Optical coherence tomography', published in *Science* 254, (1991) 1178-1181.

OCT can achieve micrometer depth resolution and allows accurate in-vivo measurement of thickness, area and volume in the tissue. In OCT, the depth dimension is explored by scanning the optical path difference (OPD) between the object path and reference path in an interferometer illuminated by a low coherence source. The maximum interference signal is obtained for OPD=0. In OCT, achievable depth resolution is given by the optical source line-width and not by the numerical aperture of the lens, as is the case in the confocal microscopy. For OPD values larger than the coherence length of the source used, the strength of the interference signal diminishes considerably. This explains the selection in depth of the OCT. Using a superluminescent diode (SLD) OCT depth resolution better than 15 μm is achievable. Employing a larger bandwidth source, 2 μm depth resolution becomes possible, as described in W. Drexler, U. Morgner, R. K. Ghanta, F. X. Kartner, J. S. Schuman, J. G. Fujimoto, "Ultrahigh-resolution ophthalmic optical coherence tomography", Nature Medicine, Vol. 7, No. 4, 502-507, 2001. OCT is an excellent method for high resolution imaging of superficial tissue, with penetration depths of up to 2-3 mm, depending on the scattering and absorption properties of the tissue.

A reflectivity depth profile called an A-scan is obtained by axial scanning. This means changing the OPD in the interferometer, for instance by moving the reference mirror in the reference arm.

B-scan images, which are analogous to ultrasound B-scan, are generated by collecting many A-scans for different and adjacent transverse positions, a method used in the paper by Huang mentioned above. The lines in the raster correspond to A-scans, i.e. the lines are oriented along the depth coordinate. The transversal scanner (operating along X or Y, or along the radius $\rho$ or the polar angle $\theta$ in polar coordinates) advances at a slower pace to build a B-scan image.

Alternatively, a B-scan can be generated by using T-scans. In this case, the transversal scanner produces the fast lines in the image, as described in the papers by A. Gh. Podoleanu, G. M. Dobre, D. J. Webb, D. A. Jackson, "Coherence imaging by use of a Newton rings sampling function," *Opt. Lett.* 21, 1789-1791 (1996), by A. Gh. Podoleanu, G. M. Dobre, and D. A. Jackson, "En-face coherence imaging using galvanometer scanner modulation," *Opt. Lett.*, 23, 147-149 (1998), and by A. Gh. Podoleanu, M. Seeger, G. M. Dobre, D. J. Webb, D. A. Jackson and F. Fitzke "Transversal and longitudinal images from the retina of the living eye using low coherence reflectometry," *J. Biomed Optics*, 3, 12-20 (1998). A T-scan can be produced by controlling either the transverse scanner along the X-coordinate, or along the Y-coordinate or along the radius $\rho$ or the polar angle $\theta$ with the other transverse and axial scanners fixed. For instance, a T-scan based B-scan is obtained by driving the X-scanner to produce T-scans while the axial scanner advances slower in depth along the Z-coordinate.

A profile of reflectivity obtained while the depth scanning is fixed is called a T-scan. C-scans are made from many T-scans along either of X, Y, $\rho$ or $\theta$ coordinates repeated for different values of the other transverse coordinate, Y, X, $\rho$ or $\theta$ respectively in the transverse plane. The repetition of T-scans along the other transverse coordinate is performed at a slower rate than that of the T-scans, called the frame rate. In this way, a complete raster is generated. Different transversal slices are collected for different depths Z, either by advancing the optical path difference in the OCT in steps after each complete transverse (XY) or ($\rho$, $\theta$) scan, or continuously at a much slower speed than the frame rate, as described in the paper by A. Gh. Podoleanu, J. A. Rogers, D. A. Jackson, S. Dunne, "Three dimensional OCT images from retina and skin", Opt. Express, Vol. 7, No. 9, 292-298, (2000), http://www.opticsexpress.org/abstract.cfm?URI=OPEX-7-9-292.

Typical errors in OCT imaging arise as a result of the specific way in which the image is constructed, i.e. from points of equal OPD, as described in the paper by M. Ohmi, K. Yoden and M. Haruna, "Optical reflection tomography along the geometrical thickness", Proc. SPIE, Vol. 4251, (2001), 76-80. Such errors are accumulated over the depth in the tissue and lead to deviations of zero OPD points from the position of the focus in confocal microscopy, as described in the paper by R. J. Zawadzki, C. Leisser, R. Leitgeb, M. Pircher, A. F. Fercher, 3D Ophthalmic OCT with a refraction correction algorithm, to be published in Proceed. SPIE, European Conf. Biomedical Optics, 22-25 Jun. 2003, paper 5140-04. The error can exceed the depth resolution achievable with Kerr lens mode-locked lasers, and in some cases, even the resolution achievable with superluminiscent diodes. The lateral errors also can amount to several pixels in the transverse section. These show that correction of images is paramount in order to obtain accurate, interpretable OCT images from the tissue. Diagnosis of glaucoma and macula degeneration relies on the instrument accuracy in determining the retina thickness. There is an increase demand for improving the resolution of the images collected.

Let us consider a curved surface separating two media of different indexes of refraction. The intersection of this surface with the plane y=0 is described by the contour $\Sigma$ in FIG. 1. For any object point O(x,z), an image point I(h,v) is generated. We orient the axes of the object space and image space along parallel directions. The ray refracted in A, intersects the object point O. The distance in the medium is AO.

Let us consider the medium homogenous of index of refraction n. The frame grabber puts the image point I in the plane (h,v) at a distance from the image point A, equal to the distance AO multiplied by the index of refraction, n. We define two errors, an axial and a lateral error. For instance, in the case of an A-scan, the user expects to collect points from along the line AI in FIG. 1, but in fact the OCT system acquires data along the line AO and places them along the line AI.

When performing a B-scan, if the normal to the surface $\Sigma$ deviates from the plane of FIG. 1, the B-scan will contain points from the volume outside the plane of FIG. 1.

For C-scanning, the user expects to collect an image from a plane II, perpendicular to the axis OZ. However, due to the curvature of the surface $\Sigma$, the coherence gate selects points from inside the object situated on a curved surface, S.

Superposing the origins of the object space and image space in point C, the lateral error $E^l$ and the axial error $E^a$ are defined as:

$$E^l = |x-h| \quad (1a)$$

$$E^a = |z-v| \quad (1b)$$

The axial error includes the elongation of the image in depth due to the index of refraction, n, of the medium or different media intersected by the ray up to the point O.

Optical coherence tomography (OCT) images are collected from the retina with different scanning procedures. The present invention relates to B-scan images, i.e. images containing the optic axis and oriented in depth. First OCT images of the retina have been produced as B-scans, constructed from many A-scans at different transverse positions. An A-scan is a profile of reflectivity in depth.

Development of en-face OCT leads to scanning the retina transversally or angularly. By putting together many T-scans for different depth positions, again a B-scan image of the tissue is obtained.

However, all images so far have been presented as rectangular, i.e. as made of line oriented laterally and axially at 90 degrees. In reality, the eye ball is round.

SUMMARY OF THE INVENTION

The present invention relates to a method wherein B-scan images or deep layers within the B-scan images are conveniently bent to represent more closely the shape of the tissue at the back of the eye.

In one aspect the invention provides a method of creating OCT cross sectional images of the retina of an eye under examination, comprising determining the length of the eye; scanning the retina with an OCT light beam in a fan configuration from a convergence point in the pupil to create an array of image points defined by a Cartesian coordinate system in an image space; transforming said array of image points in said image space to an array of points defined by polar coordinates from said convergence point in an object space taking into account the length of the eye and the refractive index within the eye; and displaying said array of points in the object space on a display device to provide an OCT cross sectional image of the retina.

The invention can compensate for distortions introduced, for example, by fan scanning, different refractive indices within the object, or depressions for the object surface. The invention is particularly applicable to OCT images of the eye, especially the human eye, in which case the layers of the retina and vitreous have different refractive indices and the fovial depression introduces further distortion.

In another aspect the invention provides a method of diagnosing diseases of the fovea, wherein the state of health of the retina in the center part is evaluated as significantly depending on the amount of elevation $\delta=(n_r-n_v)H$ of the RPE layer just below the center of the fovea.

In a further aspect the invention provides a method of generating an OCT image of a surface of an object lying in an object space, comprising scanning said surface with an incident beam to create a plurality of image points in an image space, said image space bearing a predetermined relationship to said object space that introduces distortions into the OCT image; processing said image points to compensate for said distortions caused by said predetermined relationship; and displaying said processed image points as a true image of said surface in said object space.

In yet another aspect the invention provides a method of compensating an OCT image of a surface of an object obtained with a scanning beam passing through layers of different index of refraction, comprising generating a plurality of image points with said scanning beam; processing said image points to compensate for the distortion introduced by said layers of different index of refraction; and displaying said processed image points as a true image of said surface.

In a still further aspect the invention provides a method of compensating an OCT image of the retina obtained with a scanning beam, comprising generating a plurality of image points with said scanning beam; processing said image points to compensate for the distortion introduced by layers of different index of refraction within the; and displaying said processed image points as a true image of the retina.

BRIEF DESCRIPTION OF THE DRAWINGS

The invention will now be described in more detail, by way of example only, with reference to the accompanying drawings, in which.

DETAILED DESCRIPTION OF THE PREFERRED EMBODIMENTS

OCT can be implemented, for example, with apparatus described in detail in our U.S. Pat. No. 5,975,697, the contents of which are incorporated herein by reference. The described processing can be carried out with a personal computer, for example, including a Pentium™ microprocessor.

Figure 1:
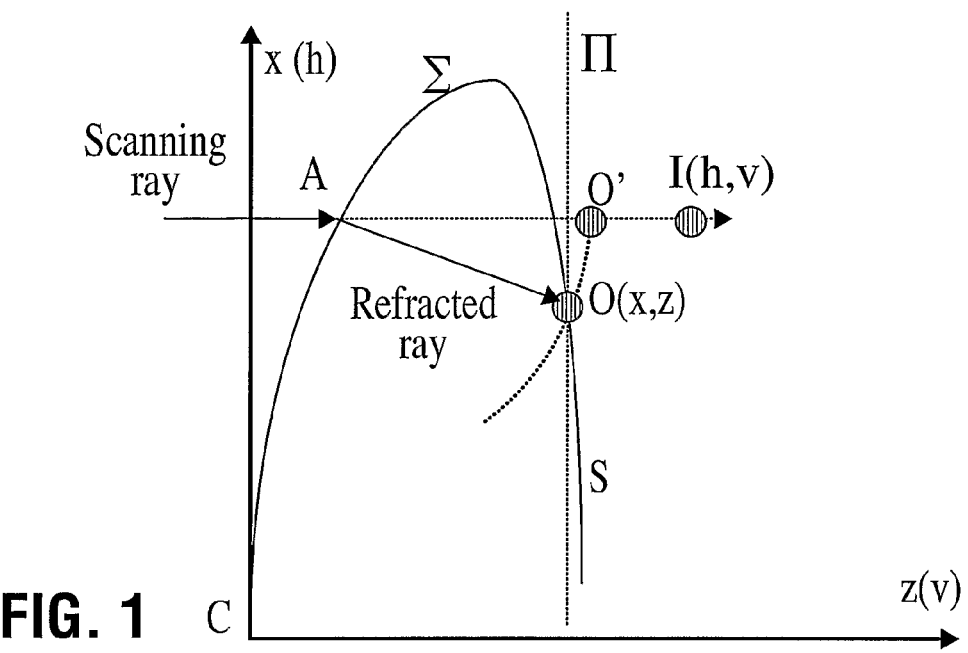
FIG. 1 shows x,z: object space; h,v: image space; Surface Σ separates media of different refractive indices; points along the line AO are placed in the image along the line AI, corresponding to a single vertical line in the generated OCT image; S: distorted surface of OPD=constant.
Figure 2:
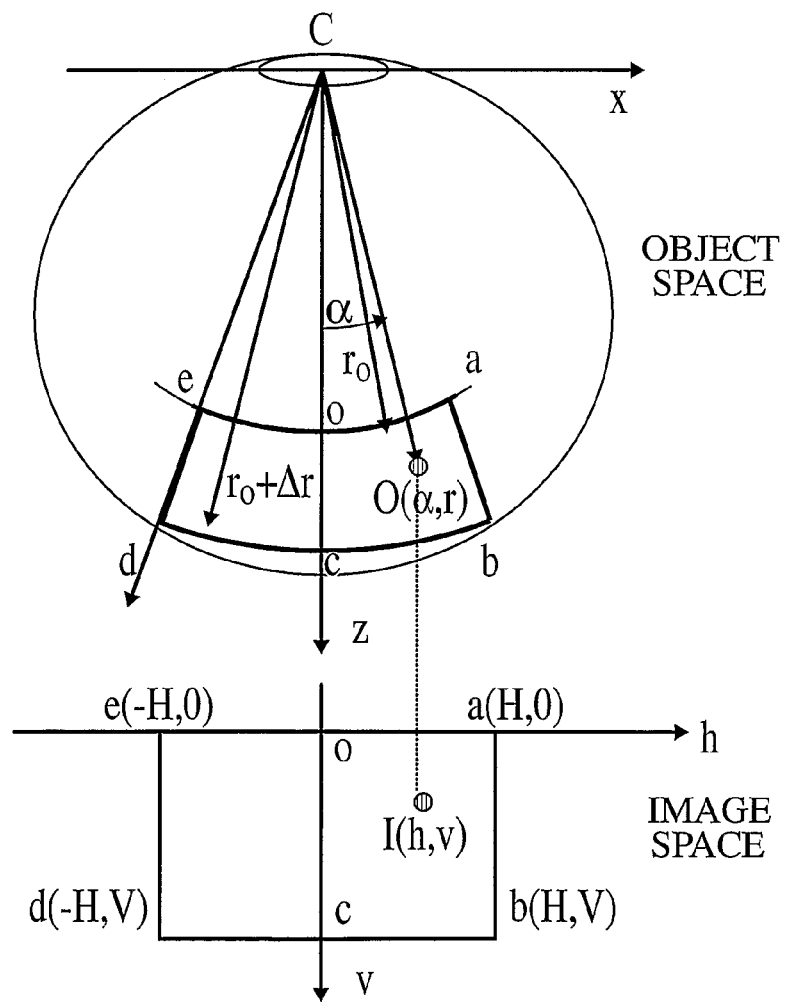
FIG. 2 illustrates the acquisition of an OCT image by fan scanning the object ray.

Consider the case of angular OCT scanning of the retina. Since, the retina must be scanned through the pupil of the eye, fan scanning must be employed. The fan of rays converges at a point C, as illustrated in FIG. 2. A collimated beam is scanned angularly through the anterior part of the eye, where refractive elements focus it on the retina. The top part of FIG. 2 shows the fan of rays scanning the retina. The bottom part represents the image acquired by the OCT for arc circles with the center in C. Polar coordinates, r, α and a corresponding Cartesian system with axes x and z are defined for the object space with the center located in the eye pupil, C. For the image space, a simple Cartesian coordinate system (h,v) is used. The relation between a point in the object space O(r, α) and the corresponding point in the image space I(h,v) needs to be understood.

The frame grabber of the OCT system places the B-scan image in the plane (h,v), where:

$$h = k_h \alpha,$$

$$v = k_v z \quad (2a,b)$$

z is the axial movement of the reference mirror from the initial position. $k_h$ and $k_v$ are scanning scaling factors for the transverse and axial scanner respectively. $k_h$ is given by the number of sample pixels along the horizontal axis, 2H, divided by the maximum optical ray deflection angle, $\alpha_M$. $k_v$ is given by the number of vertical sample pixels in the image along the vertical axis V, divided by the maximum axial range, $z_M$ covered by the axial scanner in the reference arm of the OCT interferometer.

$$k_h = \frac{2H}{\alpha_M} \quad\quad (3a, b)$$

$$k_v = \frac{V}{z_M}$$

The axial scanner varies the reference path to select points within the retina, situated at a certain radial distance between $r_0$ and $r_0+\Delta r$. If the scanner moves by z, then the coherence gated spatial window advances from the initial position $r_0$ to:

$$r = r_0 + \frac{z}{n} \quad\quad (3c)$$

where n is the average index of refraction of the retina, considered a constant, 1.38 everywhere in the eye for brevity.

Placing the reference for OPD=0 in the top centre of the image o and also making the object space and the image space coincide in this point, lateral and vertical errors produced by the fan scanning can be computed as:

$$E^l = \left(r_0 + \frac{z}{n}\right)\sin\alpha \quad\quad (4a, b)$$

$$E^a = \left(r_0 + \frac{z}{n}\right)\cos\alpha - r_0$$

$E^l$ measures how much the image point I moves laterally relative to the corresponding object point O, while $E^a$ signifies how much the image point I moves axially from the corresponding object point O. For a null $\alpha$ angle, the errors are zero.

Figure 3:
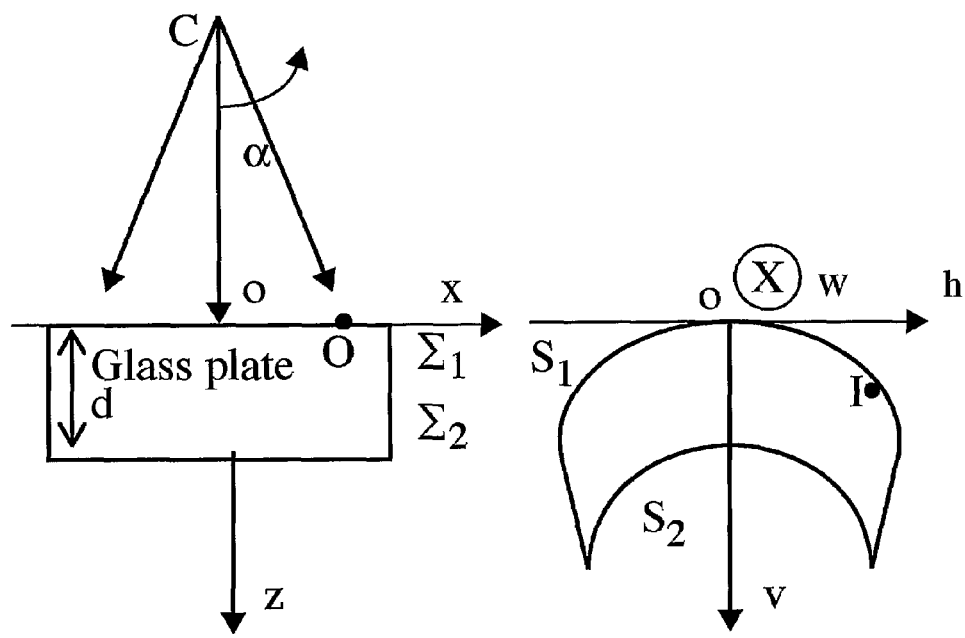
FIG. 3 shows the distorted image of a microscope slide when scanned with a fan of rays.

To better understand the distortions in the fan scanning case, let us consider a simple rectangular object, such as a microscope slide glass in FIG. 3 left. During scanning, for a certain fixed OPD in the OCT apparatus, the coherence gate selects those points from the object situated on an arc of circle with the centre in C and radius matching the reference arm length. Under these circumstances, the anterior surface $\Sigma_1$ appears in the image (FIG. 3 right) as a curved line, $S_1$. The same is true for the other surface, $\Sigma_2$ whose image is described by $S_2$. The example in FIG. 3 shows that an horizontal shape of the object surface is represented as a downward curved surface in the image space. This means that the images collected by fan scanning type have to be corrected by curving them up.

For points on the anterior surface, $\Sigma_1$, the polar coordinates in the object space are:

$$O\left(\frac{r_0}{\cos\alpha}, \arctan\frac{x}{r_0}\right) \quad\quad (5)$$

In Cartesian coordinates h and v, the points of the anterior surface $\Sigma_1$ will be located in the B-scan image at points:

$$I(h, v) = \left(k_u \arctan\frac{x}{r_0}, \frac{k_v r_0}{\cos\alpha} - k_v r_0\right) \quad\quad (6)$$

These equations show that the higher the angle $\alpha$ either side of the axis oz, the larger the vertical distortion of the image. A horizontal line in the object is represented as a downwardly curved line in the image space. Similarly, the second surface, $\Sigma_2$, given by points $$O\left(d + \frac{r_0}{\cos\alpha}, \arctan\frac{x}{r_0}\right) \quad\quad (7)$$

will be transferred to a curved line:

$$I(h, v) = I\left(k_u \arctan\frac{x}{r_0}, k_v d + \frac{k_v r_0}{\cos\alpha} - k_v r_0\right) \quad\quad (8)$$

in the image plane, (h,v). The corrected image is shown in the right hand side of FIG. 4.

We inversed equations of type 6 and 8 written for each point in the image to correct T-scan based B-scan images obtained from the retina. The correction exercise is exemplified on two images shown in FIGS. 4a and 4b, that of a normal eye and of a case of neuroretinitis with optic disc edema and peripapillary serous detachment of the neurosensory retina. To correct the images, we used an average eye length of 24 mm for a normal subject, the experimental angular span of 35° and an average index of refraction n=1.38 as presented in literature, as for example in E. Chen, Eye Laboratory, Ophthalmic Res., 25, (1993), 65-68 and in M. Hammer, D. Schweitzer, E. Thamm, A. Kolb, "Optical Properties of ocular fundus tissues determined by optical coherence tomography", Opt. Commun., 186, 149-153, 2000.

It is important to associate the pathology location to the eye curvature, which is correct in the images bent upwards. For the numerical values used, the axial error is 1.2 mm and lateral error 0.44 mm. Although it is possible to estimate the eye length, for more accurate results, OCT should be first used to evaluate the eye length value, and input to the evaluations above.

Correction of the RPE and CC Layer Orientation

A second aspect of the disclosure is the correction of orientation of layers just below the foveal pit. These layers are important for correct diagnosis of eye diseases.

Figure 4A:
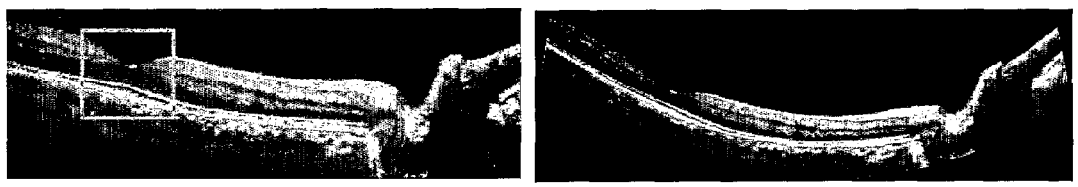
FIGS. 4a and 4b illustrate the bending images of the retina upwards to compensate for fan scanning distortion. The image in the square centred on the fovea of the normal subject is used in the processing of the RPE layer as described below.
Figure 4B:
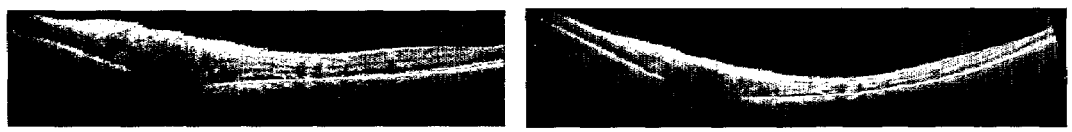

A B-scan OCT image of the fovea obtained with T-scanning is shown in FIG. 4a top left. Let us select a small lateral size image around the fovea as that inside the square superposed on the image. The lateral size is small and for simplicity, we choose to ignore here the distortion due to fan scanning presented previously. Due to the cumulated effect of (i) different indexes of refraction of the vitreous and of the retina and (ii) of the foveal depression, the image of the deep layers in the retina is distorted. For instance, an histological image of the fovea shows that the retinal pigment epithelium (RPE) is a straight oriented layer. However, due to the effects mentioned above, the RPE layer is slightly curved upwards. It is the scope of the present invention to evaluate quantitatively the distortion of the shape of the RPE layer and its upward deviation from a straight line. Let us consider the index of refraction of the vitreous, $n_v$=1.336, and of the retina up to the RPE, $n_r$=1.35.

The OCT image sampled by the square in FIG. 4a top left could be transferred to a calibrated chart containing orthogonal co-ordinate systems (ox to the right, oz downwards) or digitally sampled. The contours of the foveal pit can then be approximated by analytical curves:

$$z=f(x) \quad (19)$$

In the same system of coordinates, the equation of the middle of the RPE can be approximated by:

$$z_p = \text{cons tan tats} \quad (20)$$

The ray coming from the vitreous is incident on the retina in $A_j$. The equation of the refracted line $A_jB_j$ is written for a point $A_j$ ($x_j,z_j$) on the inner limiting membrane (ILM) described by equation (19), as:

$$x - x_j = m(z - z_j) \quad (21)$$

The slope is:

$$m = \tan\left[\frac{\pi}{2} \pm (\theta_j - \theta)\right] \quad (22)$$

The incidence angle, $\theta_j$ is $$\theta_j = \pi \pm \gamma \quad (23)$$

where $\gamma$ is given by:

$$\tan\gamma = \frac{dz}{dx} \quad (24)$$

evaluated in each point $A_j$.

Figure 5:
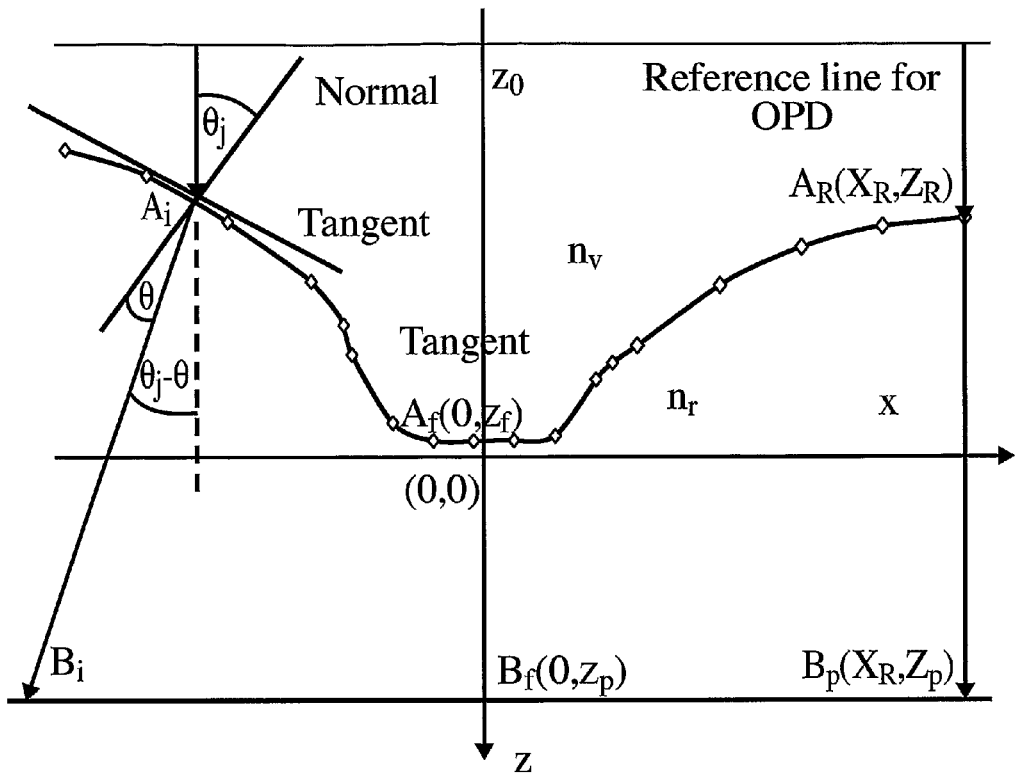
FIG. 5 shows the evaluation of the refraction angle at the interface between the vitreous and the retina.

We can calculate the coordinate of each point $B_j$ on the RPE where the line described by the equation (21) intersects the RPE described by equation (20), and obtain the points of coordinates ($x_p,z_p$). If the origin of the optical path length in the vitreous is at a coordinate $z=z_0$ (a reference line is shown in FIG. 5), then the optical path length can be evaluated as:

$$v = n_v(z_j - z_0) + n_r\sqrt{(x_j - x_p)^2 + (z_j - z_p)^2} \quad (25)$$

Figure 6:
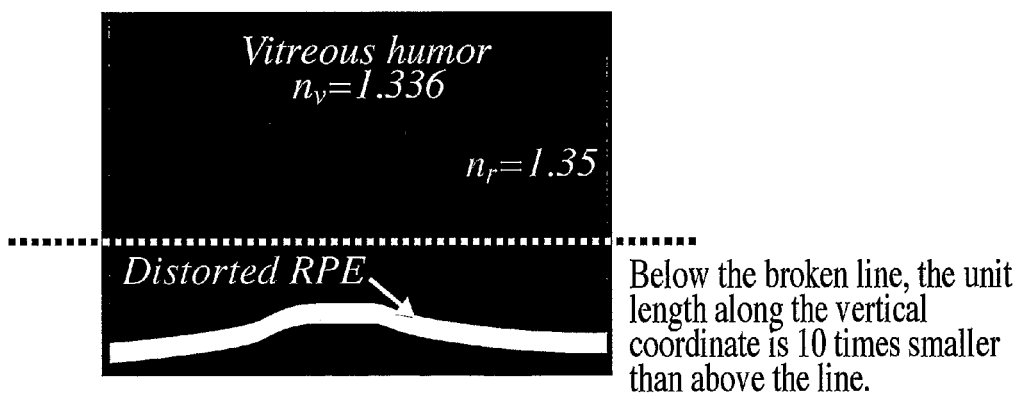
FIG. 6 is an exaggerated representation of the distortion of the RPE contour.

This determines the shape of the RPE layer in FIG. 6. The deviation of the RPE layer from straight line is small and therefore, to illustrate the distortion, the bottom part below the broken line in FIG. 6 is represented at a vertical scale multiplied 10 times.

In points such as $B_f$ and $B_p$, where the ray comes along the normal to the retina (like points in the center, $A_f$ or outside the fovea region, $A_R$ respectively), the x coordinates are the same and the optical path length is:

$$v_f = n_v(z_f - z_0) + n_r(z_p - z_f) \quad (26a)$$

or $$v_R = n_v(z_R - z_0) + n_r(z_p - z_R) \quad (26b)$$

The elevation of the RPE in the center of the image can be simply calculated by subtracting equation (26a) from (26b) which gives:

$$\delta = (n_r - n_v)(z_f - z_R) \quad (27)$$

Considering a normal average foveal pit value $H=(z_f - z_R)$=150 µm and the values for the indexes of refraction of the vitreous, $n_v$=1.336, and of the retina up to the RPE, $n_r$=1.35, $\delta$=2.1 µm. Such a deviation is hard to be noticed in FIG. 5 due to the resolution, 12 µm of an SLD based OCT system. However, this deviation is comparable to the depth resolution achievable in high resolution OCT imaging of the fovea.

The invention claimed is:

1. A method of creating OCT cross sectional images of the retina of an eye under examination, comprising:
   determining the length of the eye;
   scanning the retina with an OCT light beam in a fan configuration from a convergence point in the pupil to create an array of image points defined by a Cartesian coordinate system in an image space;
   processing said array of image points in said image space to transform said array of image points in said image space into an array of points defined by polar coordinates from said convergence point in an object space taking into account the length of the eye and the refractive index within the eye; and
   displaying said array of points in the object space on a display device to provide an OCT cross sectional image of the retina.

2. A method as claimed in claim 1, wherein said refractive index is the average refractive index of the vitreous and the retina.

3. A method as claimed in claim 1, wherein the length of the eye is measured with an OCT apparatus.

4. A method as claimed in claim 1, wherein the length of the eye is estimated.

5. A method as claimed in claim 1, wherein the images are bent upwards in object space by an amount that depends on the amount of angular scanning and the value of the length of the eye so as to accurately reproduce the curvature of the object in the displayed image.

6. A method as claimed in claim 1, wherein the retinal pigment epithelium (RPE) is scanned, and said image points are transformed taking into account the foveal pit height, H, and the index of refraction of the vitreous, $n_v$, and the average index of refraction of the fovea, $n_r$.

7. A method as claimed in claim 6, wherein the point on the RPE in the center of the fovea is lowered by $\delta=(n_r-n_v)H$ and all points either side are lowered by proportionally less value as the lateral distance up to an axis perpendicular on the fovea through the foveal pit.

8. A method as claimed in claim 7 wherein the foveal pit height H is evaluated using OCT and the indexes of refraction are $n_v$=1.336, and of the retina up to the RPE, $n_r$=1.35.

9. A method of diagnosing diseases of the fovea, comprising the steps of: creating an OCT sectional image of the retinal pigment epithelium (RPE) of an eve by scanning the retina with an OCT light beam in a fan configuration from a convergence point in the pupil to create an array of image points in an image space and transforming said array points into an object space taking into account the foveal pit height, H, and the index of refraction of the vitreous, $n_v$ and the average index of refraction of the fovea, $n_r$.
   Determining the amount of elevation $\delta=(n_r-n_v)H$ of the RPE layer just below the center of the fovea from said OCT cross sectional image of the retinal pigment epithelium; and evaluating the state of health of the retina in the center part on the basis of said amount of elevation.

10. A method as claim in claim 9, wherein during the transformation of said array of points the point on the RPE in the center of the fovea is lowered by $\delta=(n_r-n_v)H$ and all points either side are lowered by proportionally less value as the lateral distance up to an axis perpendicular on the fovea through the foveal pit.

11. A method of generating an OCT image of the retina of an eye having an object image , comprising the steps of:

scanning the retina with an incident OCT beam to create a plurality of image points in an image space, said image space bearing a predetermined relationship to said object space in accordance distortions, in the OCT image resulting from the curvature of the eye and the refractive index within the eye; processing said image points to compensate for said distortions caused by said predetermined relationship taking into account the length of the eye, the curvature of the eye, and the refractive index within the eye; and displaying said processed image points as a true image of said surface in said object space.

12. A method as claimed in claim 11, wherein the inverse of said predetermined relationship is applied to said points in said image space to compensate for said distortions.

13. A method as claimed in claim 12, wherein said scanning is fan scanning and said image points are processed to curve the image represented thereby to compensate for said distortions.

14. A method as claimed in claim 13, wherein said predetermined relationship is $$I(h, v) = I\left(k_u arc\tan\frac{x}{r_0}, k_v d + \frac{n_v r_0}{\cos\alpha} - k_v r_0\right),$$

where h, v represent the points in image space, $k_u$ and $k_v$ are scaling factors, x represents the lateral position of the point in object space, $r_0$ is the length of the scanning beam from a convergence point, and $\alpha$ is the angular displacement of the point in object space.

15. A method as claimed in claim 11, wherein said OCT image is a B-scan image.

16. A method of compensating an OCT image of the retina of an eye obtained with a scanning beam passing through layers of different index of refraction, comprising:

generating a plurality of image points with said scanning beam;

processing said image points to compensate for the distortion introduced by said layers of different index of refraction; and displaying said processed image points as a true image of the retina.

17. A method as claimed in claim 16, wherein processing also compensates for distortion introduced by fovial depression.

* * * * *